(12) United States Patent
Boehm, Jr. et al.

(10) Patent No.: US 6,972,036 B2
(45) Date of Patent: Dec. 6, 2005

(54) METHOD FOR LAMINECTOMY

(76) Inventors: Frank H. Boehm, Jr., 2408 Genesee St., Utica, NY (US) 13501; Benedetta D. Melnick, 1406 Schuyler St., Rome, NY (US) 13440

( * ) Notice: Subject to any disclaimer, the term of this patent is extended or adjusted under 35 U.S.C. 154(b) by 198 days.

(21) Appl. No.: 10/436,701

(22) Filed: May 12, 2003

(65) Prior Publication Data
US 2004/0055607 A1    Mar. 25, 2004

Related U.S. Application Data

(60) Provisional application No. 60/379,371, filed on May 10, 2002.

(51) Int. Cl.[7] .............................................. A61F 2/44
(52) U.S. Cl. ..................................... 623/17.11; 606/61
(58) Field of Search .......................... 623/17.11, 17.16, 623/908; 606/61; 128/898

(56) References Cited

U.S. PATENT DOCUMENTS

| | | | |
|---|---|---|---|
| 5,019,081 A * | 5/1991 | Watanabe .................... | 606/79 |
| 5,439,464 A * | 8/1995 | Shapiro ....................... | 606/83 |
| 6,261,582 B1 * | 7/2001 | Needham et al. ............ | 424/419 |
| 6,283,968 B1 * | 9/2001 | Mehdizadeh ................. | 606/61 |
| 6,358,254 B1 * | 3/2002 | Anderson ................... | 606/103 |
| 6,485,518 B1 * | 11/2002 | Cornwall et al. ......... | 623/17.11 |
| 2003/0004517 A1 * | 1/2003 | Anderson ..................... | 606/90 |

OTHER PUBLICATIONS

Website, anonymous Mar. 3, 2005 http://spineuniversity.com/public/spinesub.asp?id=63.*
Website, anonymous Mar. 3, 2005 http://spineuniversity.com/public/spinesup.asp?id=63.*

* cited by examiner

*Primary Examiner*—Corrine McDermott
*Assistant Examiner*—Thomas J Sweet
(74) *Attorney, Agent, or Firm*—Dilworth & Barrese LLP

(57) ABSTRACT

A process for performing lumbar laminectomy is characterized by leaving the muscles intact along the base of spinous process and posterior faces of detached portions of lamina, facet joints, and transverse processes of at least one of adjacent superior and inferior vertebrae to preserve the blood flow to the detached portions and, thus, to create a living peace of bone used as fusion material between the bases of the transverse processes of the superior and inferior vertebrae.

10 Claims, 3 Drawing Sheets

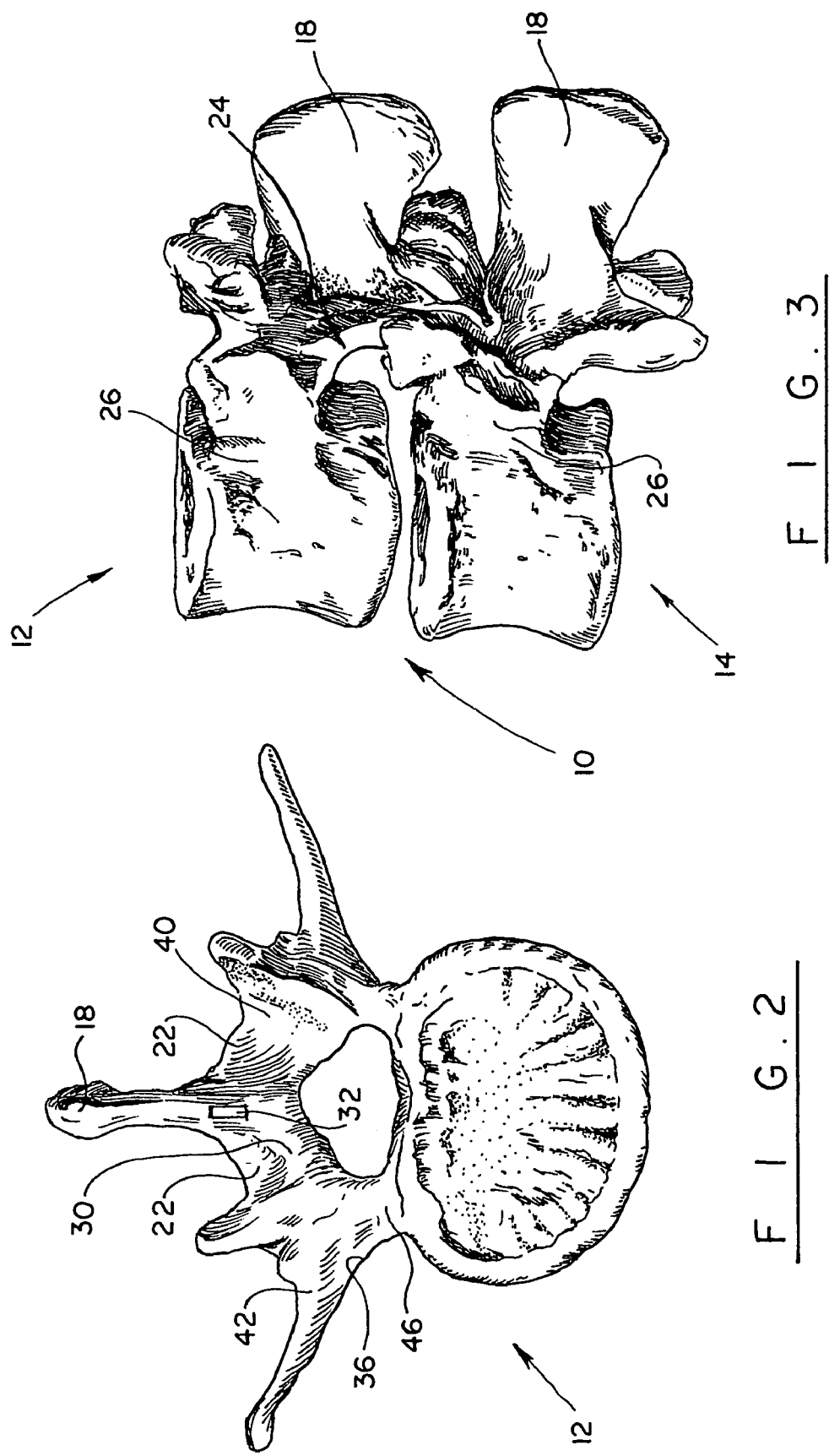

METHOD FOR LAMINECTOMY

CROSS-REFERENCE TO RELATED APPLICATION

This application is based on and claims priority under 35 U.S.C. § 1.119(e) to U.S. Provisional Application Ser. No. 60/379,371 filed on May 10, 2002 and fully incorporated herein by reference.

BACKGROUND OF THE INVNETION

1. Field of the Invention

This invention relates to techniques for the treatment of various spine diseases. Particularly, the invention relates to a spinous laminectomy procedure wherein various posterior bony structures of vertebrae to be fused continue to have a vascular supply during implantation and fusion procedures.

2. Description of the Prior Art

Lumbar laminectomy is an operation performed on the lower spine to relieve pressure on one or more nerve roots. The term is derived from lumbar (lower spine), lamina (the spinous canal's bony roof), and -ectomy (removal). Pressure on a nerve root in the lower spine causes, among others, back and leg pain. Upon removing the laminae allowing for the exposure of the compressed nerve(s), pressure is relieved by removal of the source of compression such as part of the disc, a disc fragment, a tumor, or a rough protrusion of bone.

After the pressure has been relieved, the spine should be stabilized which is typically accomplished by fusing adjacent vertebrae. Lumbar fusions have been utilized since the early 20$^{th}$ century. This surgery is traditionally accomplished via a posterior approach by making an incision along the midline of the back and down to the posterior bony elements including the spinous and transverse processes, the lamina and the facet joints.

In the classic laminectomy, musculotendinous attachments to the posterior bony elements are systematically removed, decompressing the spinous nerves and the dura. Stripping of the musculotendinous attachments is then carried laterally through the facet joints and transverse processes, and after the latter are exposed, the facet joints are partially or completely removed. Finally, the muscular attachments to the transverse processes are also stripped free.

Traditionally, the main focus of the laminectomy has been on an implant used for the fusion. The implant typically has been a bone either obtained from a bone bank, utilizing cadaveric bone, or harvested from the patient's own hip. Recently there have been several articles describing a significant long-term complication rate with hip grafting, including chronic pain, infection, and other issues. Many practitioners object to the use of cadaveric bone asserting that such a bone may not be as osteoinductive as the freshly harvested bone, due to the blood supply to the harvested bone immediately before it is removed from the hip.

Recently, the medical community has begun to discuss another important aspect of bone fusion based on the biology and nature of the posterior bony elements. This discussion is based on the recognition that if the bone to be utilized continues to have a vascular supply, the outcome of the fusion and healing process will be greatly enhanced. In the context of the spinous anatomy, the spinous processes, lamina, and transverse processes all receive a vascular supply partly from the muscles and periosteum that attach to the posterior cortical/outer surface. However, standard surgical techniques, as disclosed above, include the removal of the muscles, which may detrimentally affect the fusion procedure and lengthen the healing process.

A need therefore exists for a method that would preserve the blood flow to the spinous processes, laminae, and transverse processes while moving and relocating them to the proposed sites of fusion.

SUMMARY OF THE INVENTION

To accomplish a method meeting this need, at least a large portion of fusion material is formed from integral portions of at least one of superior and inferior vertebra to be fused. Thus, instead of obtaining either a cadaveric bone or a graft from the patient's own bones, which are dead since the blood supply is terminated the moment the bone is removed from the patient's hip, living portions of the vertebra are used as fusion material.

The living portions of the vertebra, that is those vertebral portions that receive continuous blood supply through the muscles attached thereto, are semi-detached from the rest of the vertebral structure and are plastically deformable to assume the desired shape and form. Accordingly, after the source of the pain has been removed and the space between the transverse processes of the superior and inferior vertebra has been formed, the semidetached vertebral portions are deformed to fill the formed space the vertebrae. In time, the inserted vertebral portions fuse with the juxtaposed surfaces of the transverse processes at a higher fusion rate, because the fusion material is continuously blood-supplied via the musculature coupled to the inserted vertebral portions.

The vertebral portions to be used as fusion material are formed as a result of slicing in a generally coronal plane through the base of the spinous process, lamina, facet joints and transverse processes of at least one of the superior and inferior vertebrae. Due to the inherent elasticity of the bony substance, the sliced off portions are literally peeled away in a lateral/posterior plane from the spinous process. Accordingly, each of the peeled away portions has opposite faces, one of which is what used to be the posterior surface of the vertebral elements covered by the musculature, and the opposite or inner "muscleless" face. Advantageously, the peeled away portions are so deformed that the muscleless face fills up the space between the superior and inferior transverse processes, while the posterior face with the musculature remains intact outside of the space.

As a result, the fusion material filling the space between the bases of the superior and inferior transverse processes remains a live, actually bleeding bony structure due to the muscles carried by this structure(s) during the entire fusion process.

It is therefore an object of the invention to provide a new method for lumbar laminectomy characterized by an improved rate of fusion and shortened healing process.

A further object of the invention is to provide a new process for performing lumbar laminectomy characterized by preserving blood supply to bony elements of vertebrae to be used during a fusion procedure.

Still a further object of invention is to shape and relocate the living portions of posterior bony elements of the adjacent vertebrae to be fused in a manner allowing for an improved rate of fusion.

BRIEF DESCRIPTION OF THE DRAWINGS

A detailed description of the preferred embodiment of the invention disclosing the above and other features, advantages and objects will now be described with reference to the accompanying drawings, in which:

FIG. 2 is a cranial view of a lumbar vertebra;
FIG. 3 is a lateral view of lumbar vertebrae.

DETAILED DESCRIPTION OF THE PREFERRED EMBODIMENT

Figure 1:
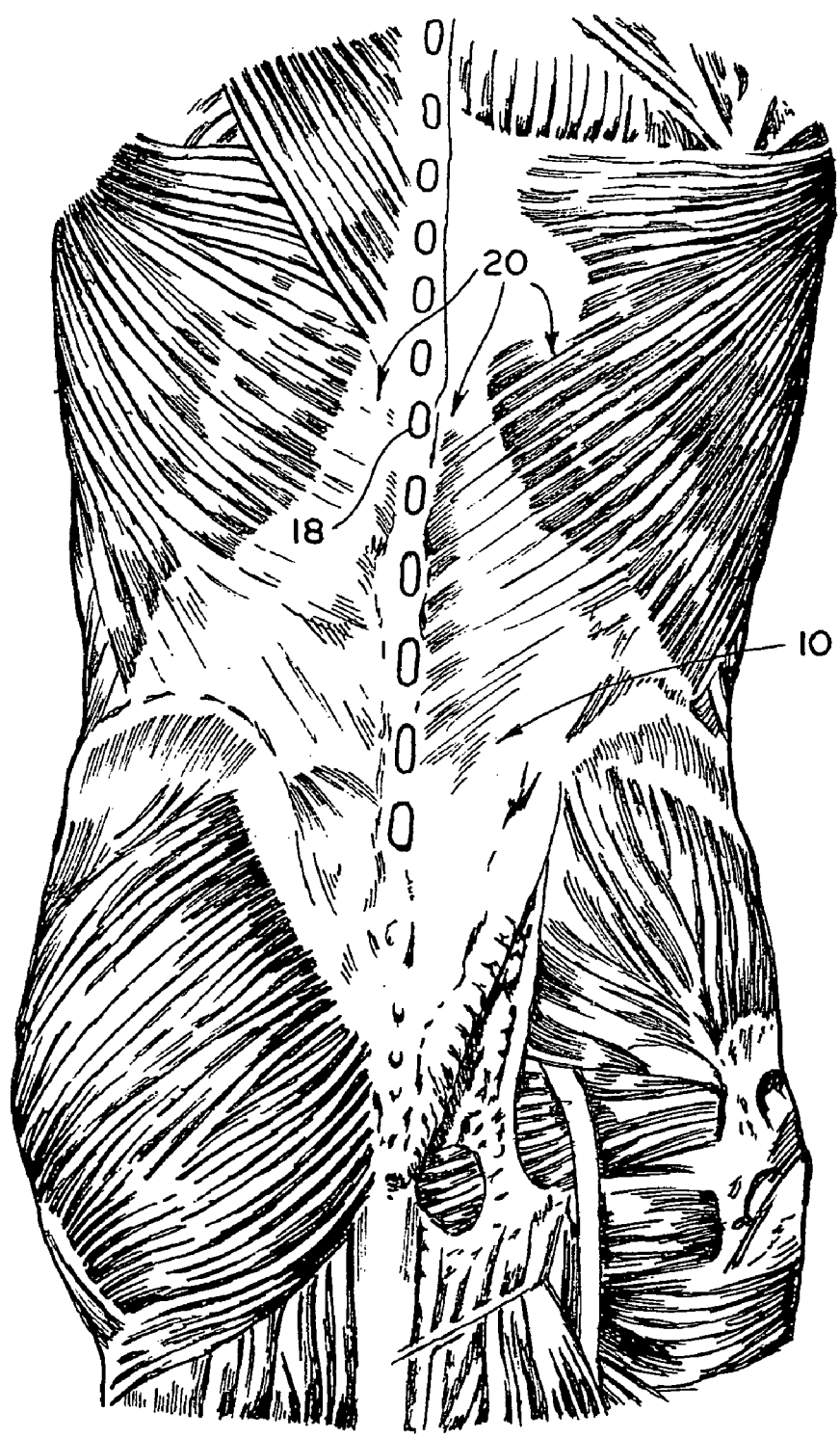
FIG. 1 is a view of muscles of the back region.
Figure 4:
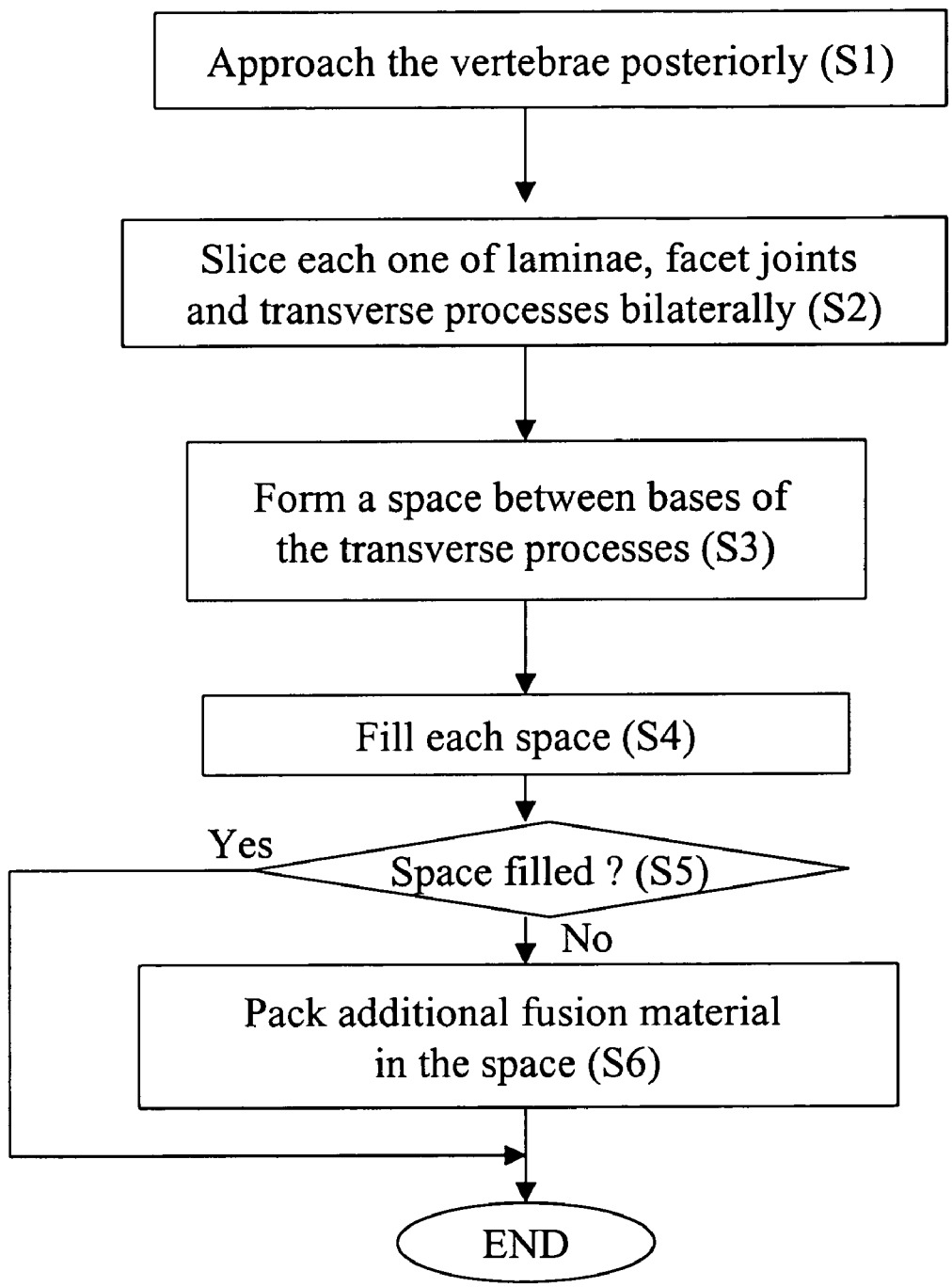
FIG. 4 is a flow chart illustrating a process for performing spinal laminectomy according to an embodiment of the present invention.

Referring to FIGS. 1–4, the inventive spine stabilizing process utilizes vascularized bone to provide vascularized autograph for enhancing fusion between bases 36 of transverse processes 26 of superior 12 and inferior 14 vertebrae of a spine 10 (FIGS. 2 and 3). A vascularized autograft obtained in accordance with a procedure disclosed herein below is obtained during a split-thickness laminoplasty technique, wherein the back of the spine is exposed but instead of removing the bony structures, they are altered in shape. The process for performing spinal laminectomy according to the embodiment of the present invention is described in more detail in FIG. 4. The process of the present invention includes following steps of posteriorly approaching the vertabrae 12, 14 in step S1, forming a space between bases 36 of the transverse process 26 in step S3, filling each space in step S4, comparing the spaced filled in step S5, and packing additional fusion material in the space in step S6. In step S5, when each space is not filled, the additional fusion material is packed in step S6.

The inventive process begins with a classical midline incision carried down to the level of a spinous processes 18 of at least one of the superior 12 and inferior 14 vertebrae. As shown in FIG. 1, muscles 20 are attached to the spinous process 18 and cover the posterior surfaces of laminae 22 (FIG. 2), facet joints 24 (FIG. 3) and transverse processes 26 supplying the blood to these bony elements. All of these elements, treated as explained below, are utilized in the present inventive method as a fusion material that is to be tucked in a space to be formed between bases 36 (FIG. 2) of the transverse processes 26 of the superior 12 and inferior vertebrae 14.

In accordance with the present invention the above-mentioned bony elements each remain with the musculature attached to a respective outer, posterior surface during a fusion procedure. In particular, after having the initial incision made, the musculotendinous attachments to the spinous processes 18 are freed to the base of these processes 30, but there is no further dissection of the musculature from the outer surfaces of the bony elements to be used as fusion material. Thus, the muscles 20 are allowed to remain intact on the opposite sides of the base 30 of the spinous process 18, lamina 22, facet joints 24, and transverse processes 26.

Next, a cutting instrument removes the base portion 30 of the spinous process 18 at the levels in which decompressive laminectomy is desired. The remaining, deeper part of the base of the spinous process is provided with a channel 32, better seen in FIG. 2 and formed in the midline of the remaining portion of the base 30 by a high-speed, hand-held drill. The shape and dimensions of the channel 32 are so selected that instrumentation, both currently available and specifically developed for the inventive method, can be easily and reliably inserted into this channel. This instrumentation would include a special hand-held and/or battery-operated oscillating saw with a disposable saw blade which is angled to follow the course of the lamina, so as to divide the latter along its anteroposterior dimension. Furthermore, this instrument is configured with a dural guard to control depth of penetration. Using the instrumentation currently available and the one configured specifically to carry out the inventive process, the lamina is divided in its so that its posterior or outer portion 40 is allowed to remain blood flow and hence, create a living piece of bone suitable for grafting. As a result, since the muscles have been detached from the base 30 of the spinous process 18, upon slicing through the lamina, the surgeon simply peels the sliced portions away from the spinous process 18. The remaining, deeper portion of the sliced through lamina can be later removed to clear access to a compressed disc.

Similarly, while maintaining the musculotendinous connections to the facet joints 24, each is divided into an anterior layer and a posterior layer provided with the musculotendinous connection attachments and reflected into the space between the bases 36 of the transverse processes 26 of the adjacent vertebrae 12, 14. Note that the lamina, facet joints and the transverse processes can be selectively sliced to form the desired amount of vascular autografts sufficient to fill the space between the bases 36 of the transverse processes 26. The surgeon may add other fusion material, which is not made from living portions of bones if the space between the bases 36 of the transverse processes 26 of the superior 12 and inferior 14 vertebrae is not satisfactory packed.

As a result, the base 36 of the transverse process 26 as it joins with the pedicle/facet complex 46 is visualized. In contrast to traditional fusion methods, the musculotendinous connection to the transverse process 26 is maintained and further used as still another living portion of bone after the transverse process is sliced similarly to the lamina and the facet joints. Thus, in addition to the living portions of the lamina 22, the peeled away living portions of the facet joint and/or transverse processes fill the space and fuse with the juxtaposed portions of the bases 36 of the transverse processes 26. Advantageously, the base 36 of the transverse process 26 is formed with a trough (not shown) which is filled with the faces of the peeled bony elements that do not have the muscles attached thereto. Accordingly, the base portions of the transverse processes 26 tend to fuse at a higher fusion rate and with fewer complications thus providing additional stabilization to the spine which has undergone lumber laminectomy.

Various modifications and improvements may be made to the present invention without departing from the scope thereof, as defined by the appended claims.

What is claimed is:

1. A process for performing spinal laminectomy comprising the steps of:
 posteriorily approaching superior and inferior vertebrae;
 bilaterally slicing at least one of laminae, facet joints and transverse processes of at least one of the superior and inferior vertebrae without detaching muscles coupled to posterior surfaces of the sliced portions of the laminae, facet joints and transverse processes;
 forming a space between bases of the transverse processes of the superior and inferior vertebrae; and
 filling each space with a respective sliced portion of the lamina, facet joint and transverse process of the at least one of the superior and inferior vertebrae, wherein the sliced portions continue to be blood-supplied via the muscles attached to the posterior surfaces of the sliced portions to improve a fusion rate between the superior and inferior vertebrae.

2. The process of claim 1, wherein the step of posteriorily approaching the superior and inferior vertebrae includes forming a midline incision carried down to a level of spinous process of the at least one of the superior and inferior vertebrae.

3. The process of claim 2, further comprising freeing musculotendinous attachments to a base of a respective one of the spinous processes, while leaving the muscles located along the base of the spinous process and the muscles attached to the posterior surfaces of the sliced portions of the laminae, facet joints and the transverse processes intact.

4. The process of claim 3, further comprising peeling the sliced portions away from the spinous process, removing inner portions of the lamina left after the sliced portions thereof have been peeled away to form access to an intervertebral space defined between vertebral bodies of the superior and inferior vertebrae.

5. The process of claim 1, further comprising removing muscles located between bases of the transverse processes of the superior and inferior vertebrae to form respective spaces.

6. The process of claim 5, further comprising filling each of the spaces between the bases of the transverse processes of the superior and inferior vertebrae with the sliced portions of the lamina, facet joint and transverse process to facilitate fusion between the bases of the transverse processes.

7. The process of claim 3, wherein the spinous process is cut to the base thereof, the process further comprising forming a channel in the base of the spinous process configured to receive instrumentation configured to slice the lamina, facet joint and transverse process in coronal planes thereof.

8. The process of claim 6, further comprising packing additional fusion material made from cadaveric bone, or harvested from a patient's hip into the space between the bases of the transverse processes.

9. A process for performing lumbar laminectomy comprising the steps of:
selectively dividing laminae, facet joints and transverse processes of at least one of superior and inferior vertebrae into an anterior portion and a posterior portion without dissecting muscles coupled to an outer face of the posterior portion;
removing muscles located between bases of the transverse processes of the superior and inferior vertebrae to form laterally spaced spaces; and
displacing the posterior portions of the at lest one of the laminae, facet joints and transverse processes into each of the spaces, whereas the displaced posterior portions continue to be blood supplied via the muscles attached to the outer faces thereof, thereby increasing a fusion rate between the superior and inferior vertebrae.

10. The process of claim 9, wherein the posterior surfaces of the lamina, facet joints and transverse processes are divided sequentially or simultaneously.

* * * * *